United States Patent [19]

Ward

[11] Patent Number: 4,518,259

[45] Date of Patent: May 21, 1985

[54] LIGHT GUIDE REFLECTOMETER

[75] Inventor: John W. Ward, Springwater, N.Y.

[73] Assignee: Eastman Kodak Company, Rochester, N.Y.

[21] Appl. No.: 401,754

[22] Filed: Jul. 26, 1982

[51] Int. Cl.³ ............................................. G01N 21/47
[52] U.S. Cl. .................................... 356/446; 250/227
[58] Field of Search ............................ 356/445–448, 356/236; 250/227; 362/31, 32

[56] References Cited

U.S. PATENT DOCUMENTS

| | | | |
|---|---|---|---|
| 3,536,927 | 10/1970 | Mink | 356/71 X |
| 3,602,213 | 8/1971 | Howell et al. | 250/227 |
| 3,676,690 | 7/1972 | McMillin et al. | 250/227 X |
| 3,709,612 | 1/1973 | Clemens | 250/227 X |
| 3,786,238 | 1/1974 | Heisner | |
| 3,992,158 | 11/1976 | Przbylowicz et al. | 426/87 X |
| 3,999,864 | 12/1976 | Mutter | 250/227 |
| 4,033,698 | 7/1977 | Demsky et al. | 250/227 |
| 4,211,469 | 7/1980 | Holzman | 350/96.16 |
| 4,219,529 | 8/1980 | Tersteeg et al. | 422/65 |
| 4,224,032 | 9/1980 | Glover et al. | 422/65 X |
| 4,239,393 | 12/1980 | Tobias | 356/419 |
| 4,246,489 | 1/1981 | Yoshida et al. | 250/577 |
| 4,258,643 | 3/1981 | Ishikawa et al. | 362/26 X |
| 4,282,560 | 8/1981 | Kringel et al. | 362/26 |

*Primary Examiner*—Vincent P. McGraw
*Attorney, Agent, or Firm*—Dana M. Schmidt

[57] ABSTRACT

There is disclosed a reflectometer comprising a one-piece molded housing that includes a radiation guide, and a source means and detector means contained within the housing, for the analysis of a test element. The guide, source means and detector means are disposed so that the detector means detects reflectance from the test element that is substantially free of specular reflectance.

13 Claims, 7 Drawing Figures

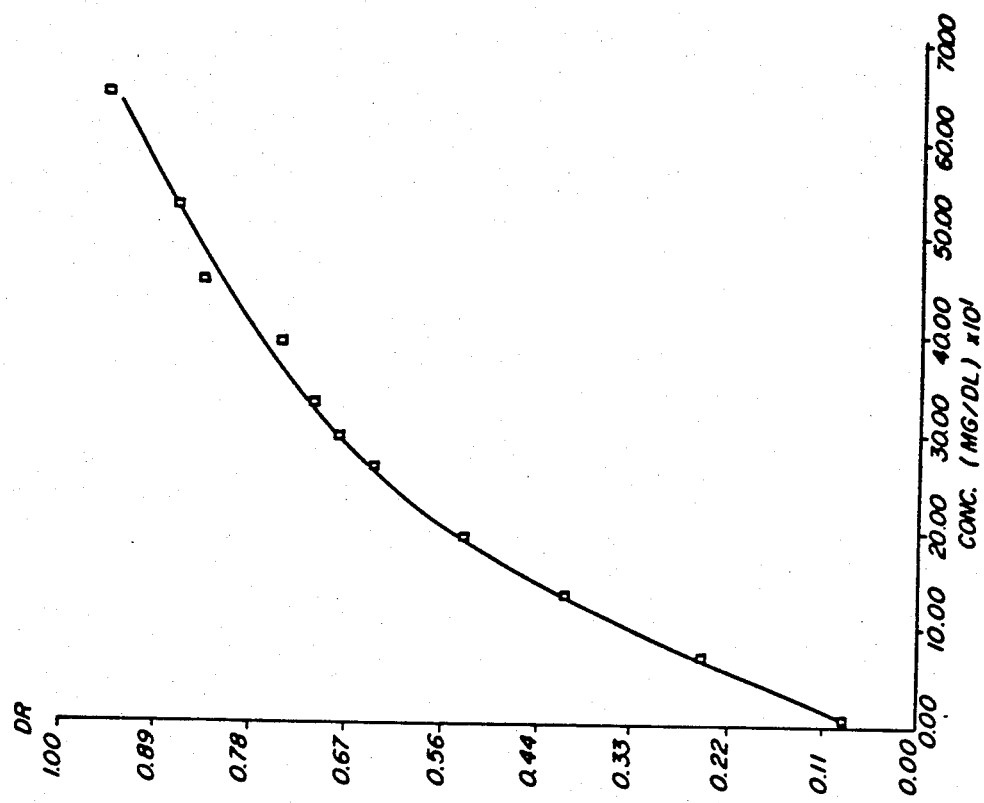
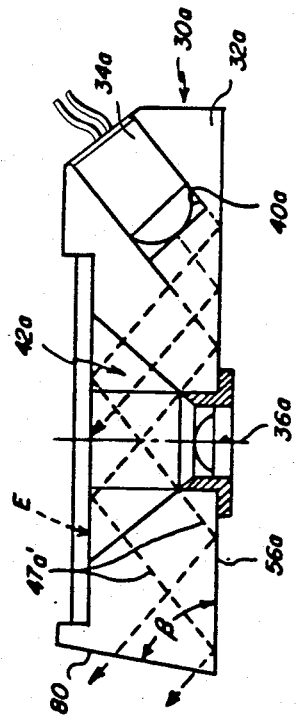
FIG. 5
FIG. 4

LIGHT GUIDE REFLECTOMETER

FIELD OF THE INVENTION

This invention relates to a reflectometer constructed to detect colorimetric densities in a test element.

BACKGROUND OF THE INVENTION

Reflectometers have been constructed featuring optical arrangements of lenses, filters, apertures, a radiation source, and detector. Examples are described in U.S. Pat. Nos. 4,219,529; issued Aug. 26, 1980 and 4,224,032, FIGS. 9 and 10; issued on Sept. 23, 1980. In such arrangements, the separate components, such as the lenses, have to be accurately located and mounted to insure proper light ray alignment and focusing.

Although such reflectometers have been successfully used, there has been a need for a simpler arrangement in which the number of components is reduced and the positioning of the components simplified. Particularly, such a need exists in the field of portable instruments, such as those used by individuals, either at home or while traveling. For example, in the case of a reflectometer used as a portable analyzer, there is a need for a reflectometer that is thin enough to fit in the user's pocket.

U.S. Pat. No. 3,536,927, issued on Oct. 27, 1970, describes a simplified reflectometer, wherein a light source and a number of detectors are mounted within a light guide. The light guide acts to direct the radiation to a plurality of emitting areas, and radiation reflected by the test object is detected.

Several disadvantages exist in devices such as are shown in the aforesaid patent. One disadvantage is that no provision is made to exclude the detection of specular reflectance. Instead, light is randomly delivered within the light guide at all angles from the light source, producing radiation that illuminates the test element at a number of angles. Because the emitted light occurs at such a variety of angles, encouraged by multiple reflections within the light guide, no provision can be made to effectively shield the detector means from specular reflectance. Specular reflection is a significant problem with test elements that have a transparent exterior surface, such as a support, that is scanned by the reflectometer. Examples of elements having such a construction appear in U.S. Pat. No. 3,992,158, issued Nov. 16, 1976. Such transparent exterior surfaces specularly reflect about 4% of the incident radiation, regardless of the absorption of light that occurs within the test element. Such specular reflection represents a significant noise factor that must be eliminated in order for highly accurate readings to be made of low-level analytes.

RELATED APPLICATIONS

Commonly owned U.S. application Ser. No. 337,189, filed on Jan. 5, 1982, by M. Snook and entitled "Fiber Optics Head Featuring Core Spacing to Block Specular Reflectance" also describes a reflectometer adapted to exclude specular reflectance from detection. However, the device described concerns the use of individual light-transporting fibers, rather than a one-piece light guide, wherein the spacing between the light-emitting fiber and the light-receiving fiber is effective to exclude specular reflectance. Such individual fibers require separate manufacture and subsequent assembly which can be eliminated by using a one-piece housing which itself provides the radiation guide means, such as is shown in U.S. Pat. No. 3,536,927. The difficulty is that the one-piece housing of the 3 927 patent lacks the desired exclusion of specular reflectance in the detected radiation.

Therefore, prior to this invention the problem has been to design a reflectometer having the simplified construction of a one-piece housing while eliminating the detection of the undesired specular reflectance.

SUMMARY OF THE INVENTION

As a solution to the above-noted disadvantages and problems, this invention provides a reflectometer, featuring a one-piece housing, that is improved to prevent detection of specular reflectance emanating from the test element.

More specifically, there is provided a compact reflectometer for the detection of density changes in a test element having a transparent exterior surface, the reflectometer comprising source means for illuminating such a test element and detector means for detecting radiation reflected from a selected portion of the test element. One-piece molded housing means are included in which said source means and said detector means are mounted. The housing means includes means for predeterminedly positioning such test element and optically transmissive radiation guide means constructed to guide the radiation to such positioned test element. The reflectometer is improved in that the source means includes means for at least partially collimating the beam of radiation and the radiation guide means includes an internally reflective surface constructed and located to direct the beam to the positioned test element. Furthermore, the detector means is located with respect to said positioning means, the source means and the reflecting surface so as to receive from an illuminated test element only radiation diffusely reflected from an illuminated test element.

Thus, it is an advantage of the present invention that the reflectometer detects reflectance from test elements having an exterior reflective surface, without detecting specular reflectance therefrom.

It is another advantage of the present invention that the reflectometer is portable, because of the compactness of the elements thereof.

It is a related advantage of the present invention that, because the reflectometer houses the optical elements in a radiation guide means, the radiation source can be mounted so as to be wholly contained within the radiation guide means, thus minimizing the thickness.

Other features and advantages will become apparent upon reference to the following Description of the Preferred Embodiments, when read in light of the attached drawings.

BRIEF DESCRIPTION OF THE DRAWINGS

FIG. 4 is a section view similar to that of FIG. 2a or 2b, but illustrating an alternate embodiment; and FIG. 5 is a graph of concentration plotted vs. reflection density, detected using the reflectometer of this invention.

DESCRIPTION OF THE PREFERRED EMBODIMENTS

The specific embodiments hereinafter described refer to a reflectometer that is particularly adaptable (a) as a portable instrument, (b) for the detection of biological analytes, that is, components of biological liquids such as serum, and (c) using light as the illuminating radiation. In addition, the reflectometer of the invention is useful to test liquids other than biological liquids, for example, industrial liquids. It is further useful as a reflectometer used to detect various color densities in non-biologic test elements, for example, photographic prints.

Figure 2A:
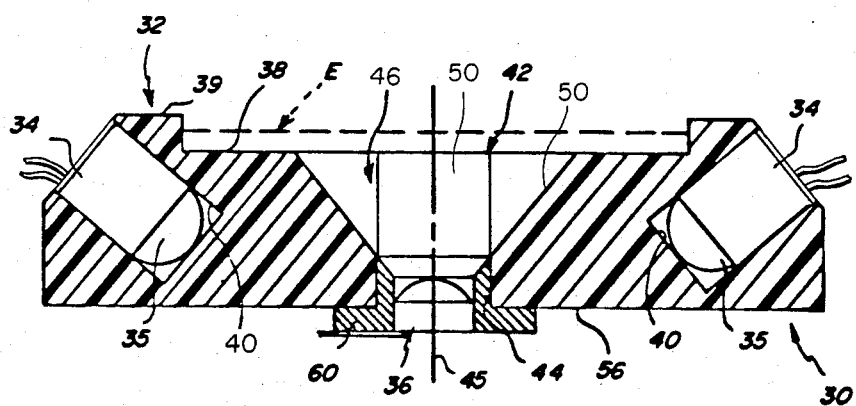
FIG. 2a is a fragmentary, vertical section view of the reflectometer, taken generally along the line II—II of FIG. 1.
Figure 3:
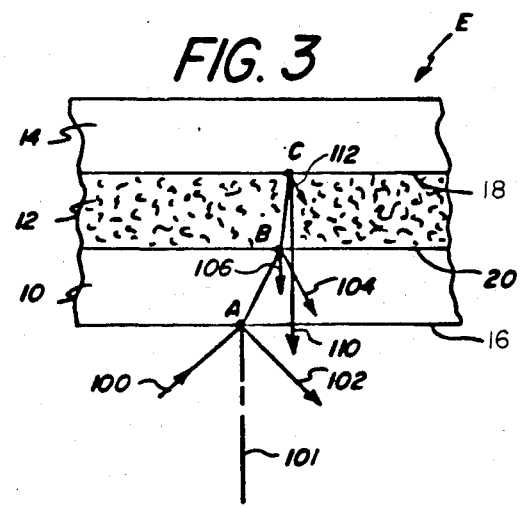
FIG. 3 is a fragmentary section view of a test element useful with the reflectometer of this invention.

The analysis of liquids, using the reflectometer of the invention, is accomplished preferably through the use of generally flat test elements E, FIGS. 2a and 3, that feature one or more liquid-containing portions mounted in a plastic frame member. The liquid-containing portions 12 and 14 are mounted on a transparent, liquid-impervious support 10, FIG. 3, having an exterior surface 16. The liquid is applied by depositing a quantity, such as a drop, onto the test element.

The layers of the test elements preferably are constructed in the manner described in, for example, U.S. Pat. No. 3,992,158, issued Nov. 16, 1976, and U.S. Pat. No. Re. 30,267, reissued May 6, 1980, the details of which are expressly incorporated herein by reference. Deposited sample liquid spreads first into layer 14, a spreading layer, and then into layer 12. Layer 14 is preferably constructed to reflect light from its interface 18 with layer 12. Preferably, layer 12 is a reagent layer and therefore the locus of the reaction that takes place that generates a detectable change. U.S. Pat. No. 4,169,751, issued on Oct. 2, 1979, discloses one useful form of such a test element.

Specular reflection or reflectance from surface 16 of element E is a noise factor of significant proportions. "Specular reflection" or "specular reflectance" is used herein in its conventional meaning, that is, reflection in which "the directions of the incident and reflected radiation make equal angles with a line perpendicular to the reflecting surface [usually called the 'normal']", McGraw-Hill *Dictionary of Scientific and Technical Terms* (1969). Therefore, specular reflection is generally to be distinguished from diffuse reflection, which latter occurs at all angles rather than just the angle of incidence.

It will be appreciated that the transparent exterior surface 16 of the test element, although the primary locus of unwanted specular reflection, is not the only such locus. That is, specular reflection occurs also at an interface 20 located between the support layer and the reagent layer, FIG. 3, as follows:

Illuminating radiation 100 directed onto test element E produces the following reflections. For any given radiation 100 that impinges onto the surface 16 of transparent support layer 10 at point A, there is a small fraction of specular reflection 102. (Line 101 is the normal to surface 16.) There is essentially no detectable diffuse reflection from point A, by reason of the high degree of transparency of the support layer. The majority of beam 100 passes through layer 10 to strike interface 20 at point B. Because there is never a perfect match of indices of refraction, some specular reflection 104 is emitted from interface 20, along with a small amount of diffuse reflection schematically indicated as arrow 106. The remaining amount of radiation 100 attempts to traverse reagent layer 12 to point C at interface 18 located between reagent layer 12 and the spreading layer 14. Because, as noted, the spreading layer 14 is highly reflective, little radiation proceeds beyond point C. Most of the radiation is diffusely reflected, schematically indicated in FIG. 3 by arrow 110. As the light passes from point B to point C and back, it traverses the particles of layer 12. To the extent those particles are radiation-absorbing dye, the diffuse component 110 is reduced proportionately. It is this diffuse component that is not absorbed that is detected as an inverse measure of the amount of dye, and therefore analyte, that is present. Conversely, specularly reflected radiations 102 and 104 never traverse the dye particles of layer 12. Therefore, for best results radiations 102 and 104 are to be excluded from detection.

There may be a slight amount of specular reflection 112 at point C, but this reflection can be ignored since it is not likely it will get past the light-absorbing dye particles that are produced in layer 12.

Figure 1:
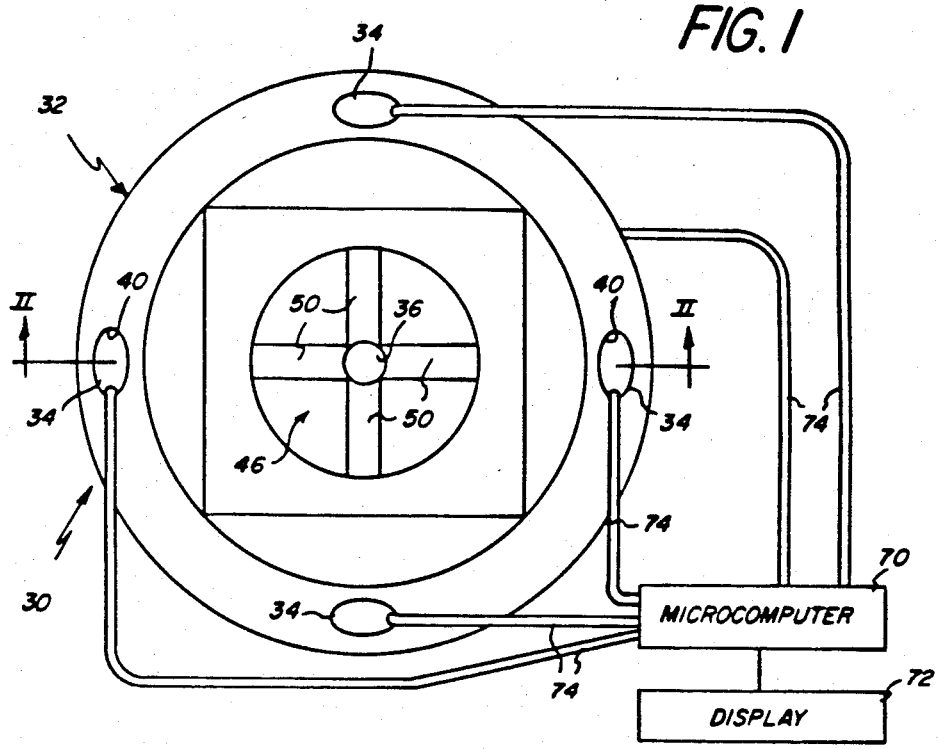
FIG. 1 is a partially schematic plan view of a reflectometer constructed in accordance with the invention, used as part of an analyzer.

It is a characteristic of this invention that radiation 110, but not specular reflections 102 or 104, is detected as follows:

Reflectometer 30, FIGS. 1 and 2a, comprises a housing 32 which preferably is itself a light guide, at least one source means 34 of illuminating radiation having a lens 35, and a detector means, such as a photodetector 36. "Light guide" as used herein means a device constructed of optically transmissive material having at boundaries intended to be internally reflective, a smooth external surface, such that light is uniformly transmitted within the material without exiting such smooth external surfaces except along paths that intersect such surfaces at a relatively steep angle. Any such radiation guide is useful regardless of whether the radiation is visible or not, if constructed to similarly direct and transmit whatever form of radiation is used. In preferred materials, light radiation enters the light guide and exits only if the exiting path forms an angle to the surface of the light guide that is at least about 45°. Various plastics are useful in making such a light guide, particularly as a molded piece. Methyl methacrylate available from Rohm Haas Co. under the trademark "Plexiglas", is a particularly useful material.

Housing 32 is provided with a portion adapted to support a test element E, shown in dotted lines, FIG. 2a. Specifically, support surface 38 is provided, preferably recessed below the uppermost surface 39 of housing 32.

Housing 32 is also provided with receptacles 40 and 42, the latter being used to mount the photodetector. Preferably, receptacles 40 are cylindrical wells with generally squared off ends 43, FIG. 2b, each sized to accommodate a single source means 34 wholly within the housing. Ends 43 need only be generally flat, as occurs in molded plastic, and only generally perpendicular to axis 48 of beam 47. Thus, slight depressions are easily tolerated in the surface forming end 43, and such surfaces are useful even if they deviate as much as 5° from being perpendicular to axis 48. However, ends 43 are preferably not curved to conform to the surface of lens 35, as such a curvature tends to scatter the collimated beam.

If several source means 34 are used, each preferably is selected to have a different wavelength of emission. Four such means are shown in FIG. 1. Any convenient source means is useful, light sources being preferred. Most preferred because of their size and wavelength selectivity are LED's. Preferably each LED is provided with a spherical lens 35, FIG. 2b, that partially collimates the emitted light into a generally cylindrical beam 47 having an axis 48, discussed further hereinafter. It will be appreciated that the more complete the collimation of beam 47, the more readily it can be controlled in the manner described herein.

Particularly useful examples of LED's include those available from So Li Co., for example those available under the designation ESBR/SBR 5501.

Receptacle 42 is divided into two portions, a lower portion 44 and an upper portion 46, and has an axis 45. Lower portion 44 is preferably cylindrical and sized to receive the photodetector. Upper portion 46 of receptacle 42 has a generally frusto-conical surface, except that planar facets 50, FIG. 1, are formed on the surface where a plane containing diametrically opposite receptacles 40, and portion 44 of receptacle 42, intersects the wall defining receptacle portion 46. Planar facets are preferred because they provide a more uniform emission of radiation from the light guide. Most preferably, facets 50 are angled so that beam 47 exits therethrough at an angle of about 90°.

Figure 2B:
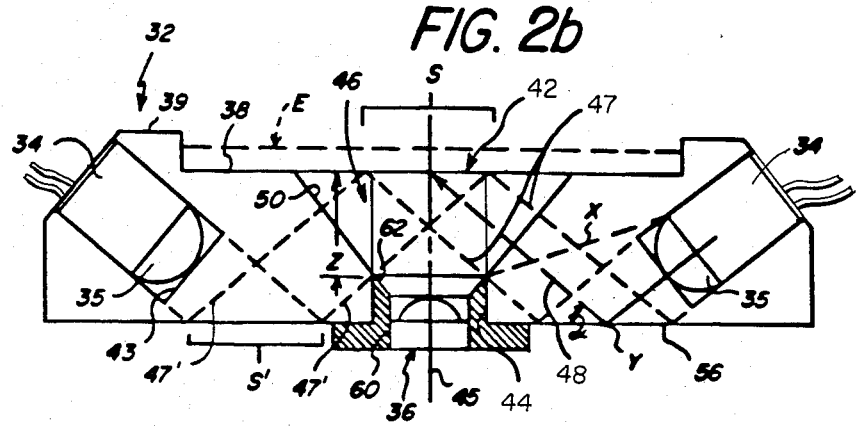
FIG. 2b is similar to the view of FIG. 2a, but with section lines removed and light ray paths added for clarity.

Depending upon the photodetector that is used, it may project more or less out the undersurface light guide 32 than is shown in FIG. 2b. Examples of particularly useful photodetectors include photodiodes available from Vactec, Inc., under the tradename VTB 1113, having an $I_L$ value of 60 μA, and an $I_D$ value of 20 pA at 2 volts.

At least the portion of the housing 32, FIG. 2b, encompassing beam 47 as it traverses from source means 34 to facet 50 of housing 32, is the light guide. It will be appreciated that, if as is preferred the light guide comprises housing 32, it provides a housing readily manufactured as a one-piece molded plastic.

The light guide further includes a reflective undersurface 56, operatively disposed between the source means 34 and photodetector 36. That is, surface 56 acts to reflect the beam 47, FIG. 2b, from source means 34 that impinges upon it. To be reflective, surface 56 is provided either with the normal smoothness of the molded plastic or with a laminated reflective material such as a metal foil. If only normal smoothness is used, angle alpha, the angle of beam 47 to surface 56, is selected in accordance with the index of refraction for the material of the light guide. For the preferred material methyl methacrylate, angle alpha is no more than about 47.8°, for smooth surface 56, to insure the light is internally reflected from, rather than emitted out of, surface 56. Most preferably, angle alpha is about 40° for methyl methacrylate. It has been found that such a smooth surface by itself is effective in providing total internal reflection of the beam.

A surprising aspect of the reflectivity of smooth undersurface 56 is that it is not adversely affected by contact with most other surfaces. The only precaution that the operator should take when using the smooth undersurface 56 as the means for reflecting beam 47, is to keep surface 56 free from contact with a material that both (a) wets surface 56 and (b) has a higher index of refraction, e.g., a piece of adhesive tape. Otherwise, the beam 47 will tend to leak into that material instead of being reflected.

Although light beam 47 is partially collimated by lens 35, a small fraction of the light may flare out along path X, FIG. 2b. Path X represents the farthest deviation from beam 47 that is also aligned with the detecting portion of detector 36. To avoid detection of such deviating light, a shield 60 is positioned around at least a portion of photodetector 36. The blocking portion 62 of the shield has a height selected to be sufficient to block path X, but insufficient to block beam 47 from reaching element E. The upper surface of portion 62 of shield 60 is preferably beveled to provide a frusto-cone of detection for photodetector 36 that coincides generally with the surfaces of upper receptacle portion 46.

To trap specular reflectance, preferably a light-absorbing material is placed diametrically opposite each source means 34, in the path of the specularly reflected beam 47′. That is, generally cylindrical beam 47 impinges upon test element E to illuminate a spot area S, FIG. 2b. The angle of beam 47 to the normal, which as shown coincides with axis 45 of receptacle 44, is (90°−α), and it is this same angle at which specular reflectance beam 47′ extends from element E. Beam 47′ also reflects off undersurface 56, at area S′. A particularly useful trap is a second source means 34 that is turned off when the first illuminating source means is activated. Preferably, such second source means is selected to emit radiation of a predominant wavelength that is different from that of the first-noted source means.

Undesired beam 47′ is not detected by photodetector 36, because photodetector 36 detects reflected light from element E, and specifically whole spot area S, as a conical beam confined within a maximum cone of detection. As noted, such maximum cone of detection preferably coincides with, or falls inside of, the general frusto-conical surfaces of upper portion 46 of receptacle 42. As is apparent from the beam paths of FIG. 2b, the horizontal positioning of the cone of detection and beam 47′ is such that all of beam 47′ passes outside the detection range of photodetector 36. The path of beam 47′ is in turn controlled by the partial collimation of beam 47, and the selected aiming of axis 48 of beam 47. The distance of reflection point Y of axis 48 on surface 56, FIG. 2b, from photodetector 36, is selected for control of the aiming. Such distance varies with the divergence, if any, of beam 47, as well as with the dimensions of the cone of detection of photodetector 36 and the spacing distance Z of the shield of the photodetector 36 from test element E, measured at the outside diameter of shield portion 62. Thus, the less the distance Z, the lesser must be the distance between reflection point Y and photodetector 36 for a given angle alpha.

Figure 2C:
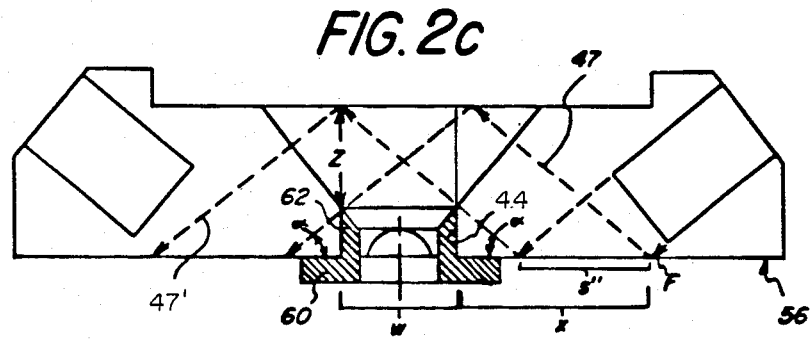
FIG. 2c is similar to the view of FIG. 2b, except that the view is further simplified to illustrate the relationship between various distances discussed herein.

Assuming that photodetector 36 is generally centered on spot S, FIG. 2b, a useful approximation of the relationship between distance Z and angle α, apparent from FIG. 2c, is $$Z = w \tan \alpha \qquad (1)$$

wherein α and Z are as described above, and w is said outside diameter. The distance "x" from the outer edge F of spot S″ to the inwardly-extending shield portion 62 is adjusted so that beams 47 and 47′ just clear shield portion 62.

The reflectometer of the invention is particularly useful in an analyzer that further includes a conventional microcomputer 70 and display means 72, FIG. 1.

Because such parts are conventional, they require no further description. Electrical connection is made from source means 34 and photodetector 36 to microcomputer 70 via any suitable connectors 74.

From the preceding, the manner in which reflectometer thickness is minimized will be apparent. Because the light guide permits the light path to be folded, the source means 34 is mountable entirely within the light guide at the side thereof. In the most preferred embodiment, source means 34 adds nothing to the thickness of the reflectometer. Thus, the entire reflectometer has a thickness from surface 39 to 56 that does not exceed about 1 cm. In contrast, if source means 34 were to be mounted through undersurface 56 to project light through a hole up to element E along axis 48, FIG. 2b, to illuminate spot area S, the source means 34 could add about 30% to the thickness of the reflectometer.

The trap for the specular reflection need not utilize an absorbing material. FIG. 4 illustrates an alternate embodiment in which the trap is constructed to direct the specular reflectance out of the reflectometer. That is, preferably the light guide is constructed so that such reflectance harmlessly exits from the light guide. Parts similar to those previously described bear the same reference numeral, to which the distinguishing suffix "a" has been added. Thus, reflectometer 30a comprises a housing 32a, which is itself the light guide, and source means 34a and photodetector 36a mounted in receptacles 40a and 42a as before. However, in this embodiment there is no inactive source means diametrically opposite receptacle 40a to act as a light trap. Instead, side surface 80 of light guide 32a is free of any contained electrical device and is inclined at an angle beta to undersurface 56a. The value of beta is selected to insure that specular reflectance beam 74a' exits out of surface 80, rather than internally reflects from it. The particular value will again depend upon the index of refraction for the light guide. In the case of methyl methacrylate, beta is preferably less than 92°, and most preferably about 75°. A value greater than 92° for beta is undesirable because it would tend to internally reflect the specular reflectance 47a', probably back to photodetector 36a.

EXAMPLE

FIG. 5 illustrates the ability of the reflectometer of this invention to detect varying degrees of concentration as a function of inversely proportional densities produced in appropriate test elements. Specifically, test elements constructed as described in U.S. Pat. No. 3,992,158 were spotted with a 10 μl drop of calibrator liquid containing twelve different known levels of concentration of glucose. The densities measured as $D_R$ were noted, using a reflectometer constructed as shown in FIGS. 1 and 2b, and plotted for those concentrations. The calibrator curve of FIG. 5 was the result, demonstrating that a proportionally increasing density was detected at increasing concentrations of glucose.

The invention has been described in detail with particular reference to preferred embodiments thereof, but it will be understood that variations and modifications can be effected within the spirit and scope of the invention. For example, the invention is also applicable to a reflectometer that is not portable.

What is claimed is:

1. In a reflectometer adapted for measuring non-uniform distribution of density and comprising source means for generating radiation suitable to illuminate a test element, detector means for detecting radiation reflected from such test element, and one piece molded housing means in which said source means and said detector means are mounted, said housing means including as portions integral therewith, means for predeterminedly positioning such test element and optically transmissive radiation guide means constructed to guide said radiation from said source means to be positioned test element, the improvement wherein (i) said source means includes means for at least partially collimating said illuminating radiation, (ii) said radiation guide means includes an internally reflective surface constructed and located to direct said beam to illuminate a selected portion of a positioned test element, and (iii) said detector means is located with respect to said positioning means, said source means and said reflecting surface so that the test element is illuminated by a whole spot of light that is disposed approximately centered above said detector means, and said detector means receives from an illuminated test element only radiation diffusely reflected from the illuminated test element.

2. In a reflectometer adapted for measuring non-uniform distribution of density and comprising source means for generating illuminating radiation; detector means for detecting radiation reflected from a test element; one piece molded housing means in which said source means and said detector means are mounted, said housing means including as portions integral therewith, a support for such test element and optically transmissive radiation guide means disposed between said source means and said test element support constructed to direct said illuminating radiation onto said supported test element;

the improvement wherein (i) said source means is constructed to deliver at least a partially collimated beam of radiation, (ii) said guide means includes an internally reflective surface optically disposed to direct said beam to illuminate a selected portion of said test element, and (iii) said detector means is disposed with respect to said support, said source means and said reflective surface so that the test element is illuminated by a whole spot of light that is disposed approximately centered above said detector means, and said detector means receives from said illuminated element only reflected radiation substantially free of specular reflectance of said beam.

3. A reflectometer as defined in claim 1 or 2, and further including means for trapping specular reflectance emanating from an illuminated test element.

4. A reflectometer as defined in claim 3, wherein said trapping means includes an inactivated source means for generating illuminating radiation, a portion of said guide means being disposed to direct said specular reflectance to said inactivated source means.

5. A reflectometer as defined in claim 1 or 2, wherein said reflective surface comprises a generally planar, smooth exterior surface of said guide means, disposed to reflect said illuminating radiation received from said source means.

6. A reflectometer as defined in claim 1 or 2, wherein said source means includes a lens that directs said illuminating radiation as said partially collimated beam.

7. A reflectometer as defined in claim 1 or 2, wherein said source means is mounted wholly within said housing means so as to minimize the thickness of said reflectometer.

8. A reflectometer as defined in claim 1 or 2, wherein said guide means is constructed to direct specular reflectance out of said reflectometer.

9. A reflectometer as defined in claim 1, wherein said guide means is said housing.

10. A reflectometer as defined in claim 1, wherein said guide means has surfaces extending from said detector means to said positioning means, angled so that said beam exits one of said surfaces at an angle of about 90° before illuminating a positioned element.

11. A reflectometer as defined in claim 2, wherein said guide means has surfaces extending from said detector means to said test element support, angled so that said beam exits one of said surfaces at an angle of about 90° before illuminating said supported test element.

12. A reflectometer as defined in claim 1 or 2, and further including shield means disposed around at least a portion of said detector means for blocking all line-of-sight radiation from said source means to said detector means.

13. A reflectometer as defined in claim 12, wherein the distance Z between said shield means and said illuminated test element, measured from the outside diameter of the light-blocking portion of said shield means, is the value determined by the equation $Z = w \tan \alpha$ wherein w is said outside diameter and $\alpha$ is the angle at which said beam is reflected from said reflective surface.

* * * * *